Figure 2A:
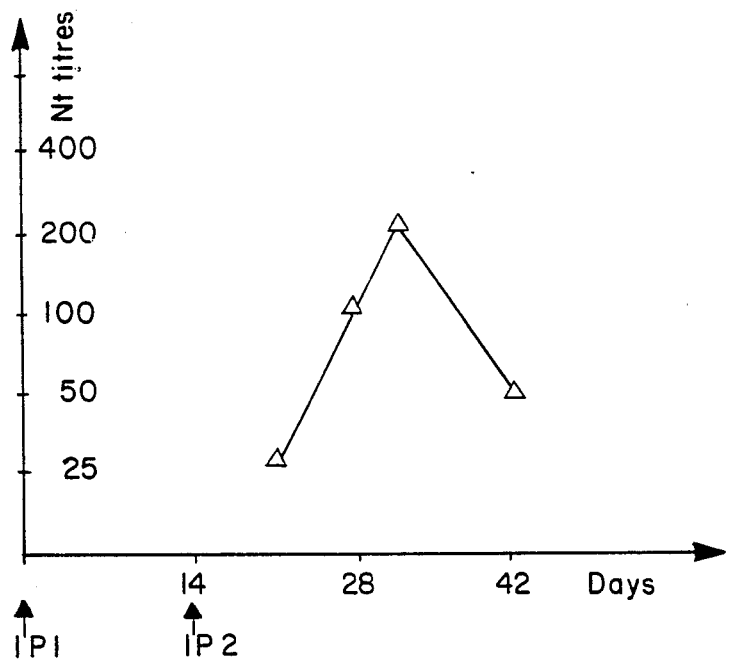

United States Patent [19]

Quash et al.

[11] Patent Number: 4,965,069

[45] Date of Patent: Oct. 23, 1990

[54] OXIDIZED VIRUSES OR VIRAL ANTIGENS AND UTILIZATION FOR DIAGNOSTIC PROPHYLACTIC AND/OR THERAPEUTIC APPLICATIONS

[76] Inventors: Gerard A. Quash, 12 Alle'des Charmilles, Franche Ville, France, 69340; John D. Rodwell, 430 Ramsey Rd., Yardley, Pa. 19067; Thomas J. McKearn, R.D. #3, Box 119, New Hope, Pa. 18938; Jean P. Ripoll, 12 rue Freres Rizier, Cassieu, France

[21] Appl. No.: 52,518

[22] Filed: May 20, 1987

Related U.S. Application Data

[63] Continuation-in-part of Ser. No. 928,631, Nov. 18, 1986, Pat. No. 4,853,326.

[51] Int. Cl.⁵ ............................................. A61K 39/12
[52] U.S. Cl. ..................................... 424/89; 435/238
[58] Field of Search ............................ 424/89; 435/238

[56] References Cited

U.S. PATENT DOCUMENTS

| | | | |
|---|---|---|---|
| 3,326,767 | 6/1967 | Holper et al. | 424/89 |
| 3,839,555 | 10/1974 | Billiau et al. | 424/89 |
| 4,196,265 | 4/1980 | Koprowski et al. | 435/7 |
| 4,217,338 | 8/1980 | Quash | 436/543 |
| 4,355,102 | 10/1982 | Quash | 435/5 |
| 4,356,170 | 10/1982 | Jennings et al. | 424/88 |
| 4,367,309 | 1/1983 | Kondo et al. | 435/188 |
| 4,419,444 | 12/1983 | Quash | 435/7 |
| 4,634,666 | 1/1987 | Engleman et al. | 435/68 |

FOREIGN PATENT DOCUMENTS

| | | |
|---|---|---|
| 0663229 | 5/1963 | Canada . |
| 0088695 | 9/1983 | European Pat. Off. . |
| 0117657 | 9/1984 | European Pat. Off. . |
| 0122841 | 10/1984 | European Pat. Off. . |
| 2378094 | 1/1977 | France . |
| WO84/04327 | 11/1984 | PCT Int'l Appl. . |
| 86/03224 | 6/1986 | PCT Int'l Appl. . |

OTHER PUBLICATIONS

Davis et al., *Microbiology,* Fourth Edition, J. B. Lippincott Company, Philadelphia, 1990, p. 890.
Prince et al, *Journ. Virol.,* 57, 721–728, 1986.
Murphy et al., *Journ. Clin. Microbiol.,* 24, 197–202, 1986.
Schlesinger, *Virology Monograms,* 16, Springer-Verlag, New York, 1977, pp. 1–132.
Means et al., *Chemical Modification of Proteins,* Holden Day Inc., 1971, pp. 126–127.
Johnson et al., *Journ. Biol., Chem.,* 234, 4022–4026, 1979.
Hallum et al., *Virology,* 12, 283–308, 1960.
Barrett, *Textbook of Immunology,* Third Edition, The C. V. Mosby Company, Saint Louis, 1978. pp. 294–300.
Gerschenfeld, *American Journ. Pharmacy,* 135, 278–287, 1963.
Dresman et al., *Virology,* 69, 700–709, 1976.
Berman et al., 1985, Trends in Biochem. 3:51–53.
Finegold et al., 1978, in Baley and Scott's Diagnostic Microbiology, 5th ed., The C. V. Mosby Company, pp. 272–278.
Glorioso et al., 1983, Virol. 126:1–18.
Hagenarrs et al., 1983, J. Virol. Meth. 6:233–239.
Krech et al., 1971, Z. Immun. Forsch. Bd. 141:S411–429.
Lee et al., 1984, Proc. Nat'l Acad. Sci. USA 81:3856–3860.
Peake et al., 1982, J. Virol. 42(2):678–690.

*Primary Examiner*—Sam Rosen
*Assistant Examiner*—David A. Saunders
*Attorney, Agent, or Firm*—Pennie & Edmonds

[57] ABSTRACT

Novel and improved methods for diagnosis, prognosis, prophylaxis and therapy of viral infections are described. The novel methods employ a virus, viral antigen or fragment thereof in which "perturbation" of an oligosaccharide moiety renders the virus, viral antigen or fragment thereof more specifically recognizable or reactive with neutralizing antibody. As described, "perturbation" of an oligosaccharide moiety encompasses a variety of modifications such has one that (1) alters the chemical or physical structure of a carbohydrate residue that is naturally present; (2) that removes, wholly or in part, a carbohydrate residue; and/or (3) that prevents or alters addition of a carbohydrate residue. A variety of different methods for oligosaccharide "perturbation" are also described. In particular, the carbohydrate residue is altered by an oxidizing agent.

14 Claims, 3 Drawing Sheets

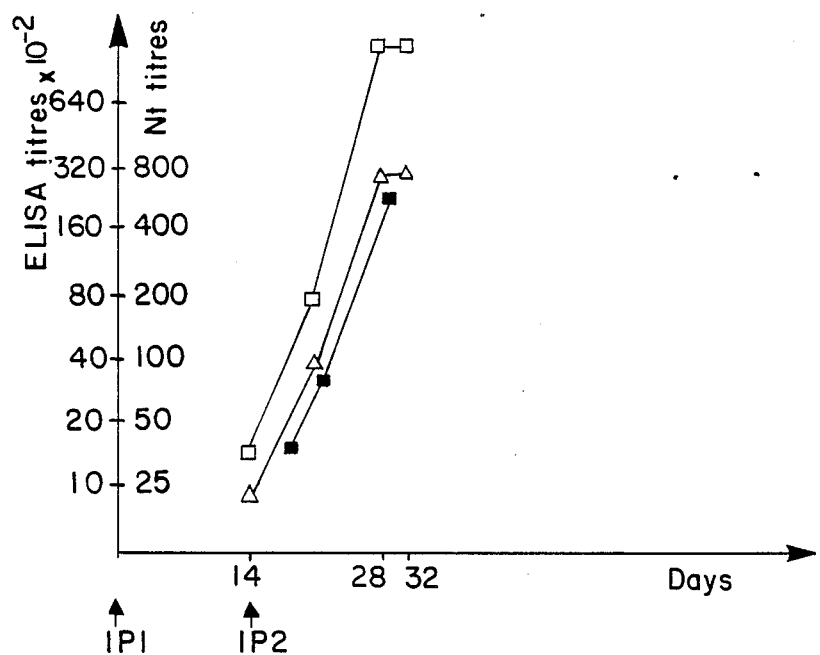
FIG. IA  Untreated virus
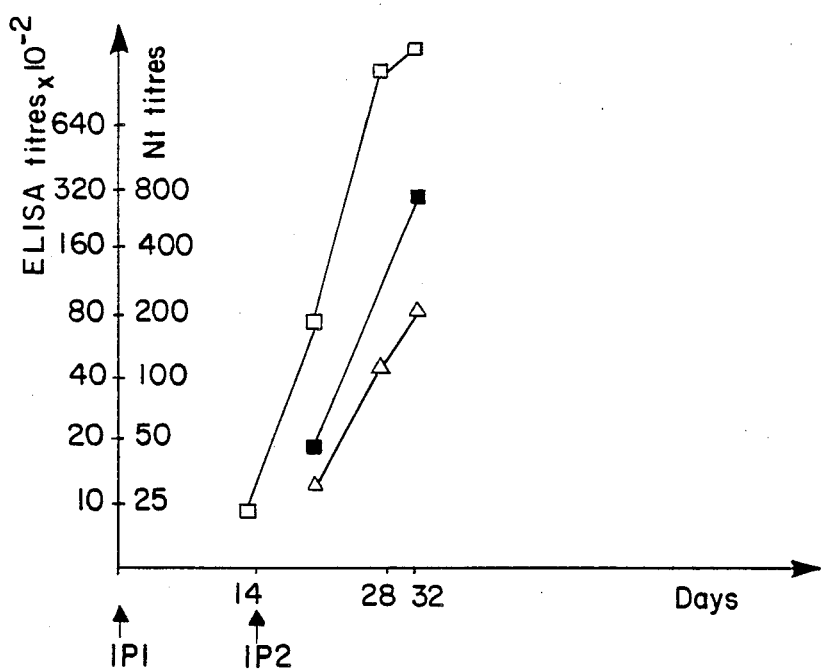
FIG. IB  Oxidized virus

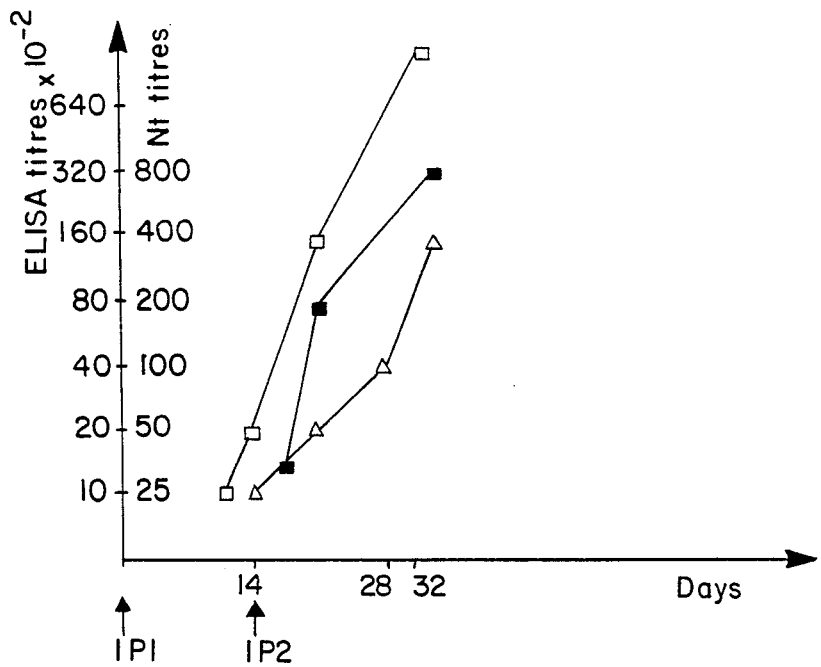
FIG. 1C    Inactivated virus
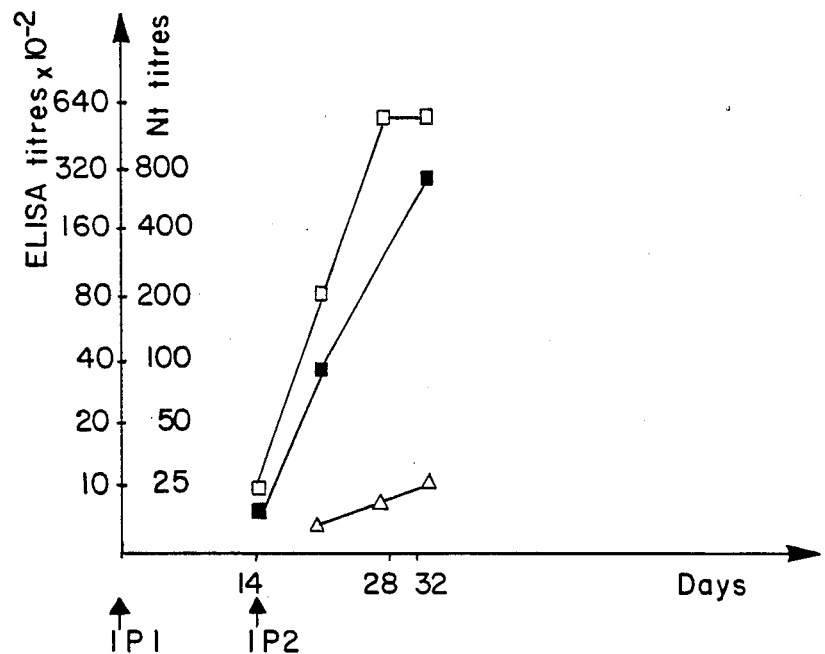
FIG. 1D    Inactivated - oxidized virus

OXIDIZED VIRUSES OR VIRAL ANTIGENS AND UTILIZATION FOR DIAGNOSTIC PROPHYLACTIC AND/OR THERAPEUTIC APPLICATIONS

This application is a continuation-in-part of U.S. application Ser. No. 928,631, filed Nov. 18, 1986, now Pat. No. 4,853,326.

1. FIELD OF THE INVENTION

The present invention relates generally to novel and improved methods for diagnosis, prophylaxis and therapy of viral infections. More particularly the invention relates to novel methods employing a virus, viral antigen or fragment thereof in which an oligosaccharide moiety is perturbed in such a way that the virus, viral antigen or fragment thereof is specifically recognized by or reacts specifically with neutralizing antibodies. The term "perturbed" oligosaccharide moiety is intended to encompass a variety of different types of modifications such as a modification (1) that alters the chemical or physical structure of a carbohydrate residue that is naturally present; (2) that removes, wholly or in part, a carbohydrate residue that is naturally present; and/or (3) that prevents or alters the addition of a carbohydrate residue (i.e. prevents or alters glycosylation).

The perturbed viruses, viral antigens and fragments thereof prepared according to the present invention are useful for in vitro diagnostic and prognostic applications as well as for in vivo prophylactic and therapeutic applications.

2. BACKGROUND OF THE INVENTION

Viruses are important etiological agents of a wide variety of diseases. In animals the immune response comprises one of the basic mechanisms to fight viral infections. Classically, the immune response encompasses two facets: the B-lymphocyte antibody response, referred to as humoral immunity and a T-lymphocyte-mediated response, known as cell-mediated immunity. The present application is concerned particularly with the antibody response.

While specific antibody of classes IgG, IgM and IgA can bind to any accessible epitope on a surface protein of a virion, only those antibodies which bind with reasonably high avidity to particular epitopes on a particular protein in the outer capsid or envelope are capable of neutralizing the infectivity of the virion. These are termed "neutralizing antibodies." "Neutralization" as used throughout the instant specification is intended to include not only (1) classical virus neutralization which results when antibody binds to a surface antigen of a virion which ordinarily binds to a receptor on the surface of a susceptible cell and thereby prevents infection of a susceptible cell or leads to opsonization but also includes (2) interactions such as the binding of an antibody to neuraminidase of influenza virus (IF) which results in inhibition of release of progeny virus particles from the plasma membrane of infected cells and slows virus spread and (3) binding of an antibody to fusion protein (F) of paramyxoviruses which does not prevent initiation of infection but does block the direct cell to cell spread of newly formed virions once infection has been established.

Antibodies directed against irrelevant or inaccessible epitopes of surface proteins, or against internal proteins of the virion, or virus-coded non-structural proteins, such as virus-encoded enzymes can sometimes exert indirect immunopathological effects, but may play no role in elimination of the infection. These are "non-neutralizing antibodies." In fact, certain non-neutralizing antibodies not only form damaging circulating "immune complexes" but may actually impede access of neutralizing antibody and enhance the infectivity of the virion for some cells. For example, in the presence of sub-neutralizing concentration of neutralizing antibody or excess of non-neutralizing antibodies viruses such as togaviruses are actually taken up more efficiently by macrophages (via Fc receptors on the macrophage to which the virus-antibody complex binds). The virus multiples intracellulary to high titer inside the macrophages. Hence the non-neutralizing antibodies act as "enhancing antibody." Specific examples of such viruses include dengue virus types 1–4.

Thus in response to a viral infection, two very different kinds of antibodies are produced: neutralizing antibodies and non-neutralizing antibodies. Each is present in the serum of infected individuals or individuals previously exposed to a virus or a viral antigen in varying amounts. In order to assess the true immunocompetent status of an individual it is necessary to know the absolute and relative amounts of both neutralizing and non-neutralizing antibodies. Yet conventional serological assays of antiviral antibodies do not, and in fact cannot, distinguish these two kinds of antibodies. Conventional serological assays measure the presence of both types of antibodies. Hence there is no serological method for measuring or assessing the true immune status or immunocompetence of individuals.

The only conventional method for assessing virus neutralizing ability of serum of individuals has been the virus neutralization assay such as that described by Krech et al., Z. Immuno., Forsch. Bd. 141 S: 411–29 (1971). Neutralization assays require: (1) use of infectious virus and (2) cell culture techniques. Such assays are slow, cumbersome, labor intensive and expensive. Hence there has been a long-felt need for a rapid, inexpensive accurate serological method to assess the immunocompetent status of individuals.

Examples of specific situations in which a rapid, easy test for assessing the immunocompetence of an individual is particularly important include, but are not limited to, the following. Firstly, exposure of a pregnant female to a virus such as rubella virus or cytomegolovirus poses significant risk of congenital defects for the fetus. Using conventional serological methods such as ELISA assays the titer of all IgM and IgG antibodies against the relevant virus, both neutralizing and non-neutralizing, may be determined. If the total IgM level is elevated indicating that the response is due to reaction by a presumably "naive" immune system, a therapeutic abortion will be recommended because it is unlikely that neutralizing antibodies against the virus are present. If, however, only the total IgG level is elevated, no therapeutic abortion will be recommended because the test cannot distingush whether the IgG's present are neutralizing or non-neutralizing antibodies. The patient is faced with a long stress-filled pregnancy which may end in a child with congenital defects.

Secondly, exposure of (or reactivation of previous infection associated with immunosuppression) organ transplant or bone marrow transplant patients to viruses such as cytomegalovirus (CMV) poses significant risks of clinical disease states including pneumonia, hepatitis, retinitis, encephalitis, etc. Moreover, the glomerulopathy induced by CMV adversely affects the survival of kidney grafts, so that renal transplant patients face additional life-threatening organ rejection [see generally, White et al., eds., in Medical Virology, 3d ed., Academic Press, Inc., New York, pp. 419–426 (1986)].

Thirdly, viral infections pose significant, indeed often life-threatening risks for immuno-suppressed patients including cancer patients undergoing chemotherapy, and those afflicted with either congenital or acquired immunodeficiency such as acquired immune deficiency syndrome (AIDS).

Fourthly, certain viral infections endemic to specific geographic areas pose significant risks, for example, for military or diplomatic personnel stationed in these areas. Specific examples include but are not limited to Rift Valley fever, dengue etc. Vaccines may protect by actively eliciting the production of neutralizing antibodies. Evaluation of the immunocompetent status of personnel to be sent to these areas following vaccination is important.

In all the above examples, there is a need for rapid, serological methods for determining both the presence and titer of virus neutralizing antibodies. Examples of formats useful in such rapid, serological methods include but are not limited to Enzyme-Linked Immunosorbent Assays (ELISA), radioimmunoassays (RIA), immunofluoresence or other fluorescence-based assays, agglutination assays, etc.

Hagenaars et al., J. Virol. Methods 6: 233–39 (1983) described a modified inhibition ELISA assay which showed some correlation between ELISA titers and neutralization assay titers for polio virus type I. Unlike the presently described assays, however, the modified inhibition ELISA of Hagenaars et al. was more complex and cumbersome.

Dreesman et al., Virol. 69:700–09 (1976) investigated the site associated with hemagglutinating activity of adenovirus following oxidation of viral antigen and purified virus preparations. Animals immunized with oxidized preparations showed significantly decreased haemgglutination — inhibiting antibody; however, neutralizing antibody titers were not substantially affected. In contrast, according to the present invention, mild oxidation of the oligosaccharide moiety of virus, viral antigen and virus fragments not only enhances the ability of the immunogen to elicit neutralizing antibody production, but more critically also elicits a protective immune response.

3. SUMMARY OF THE INVENTION

Figure 2B:
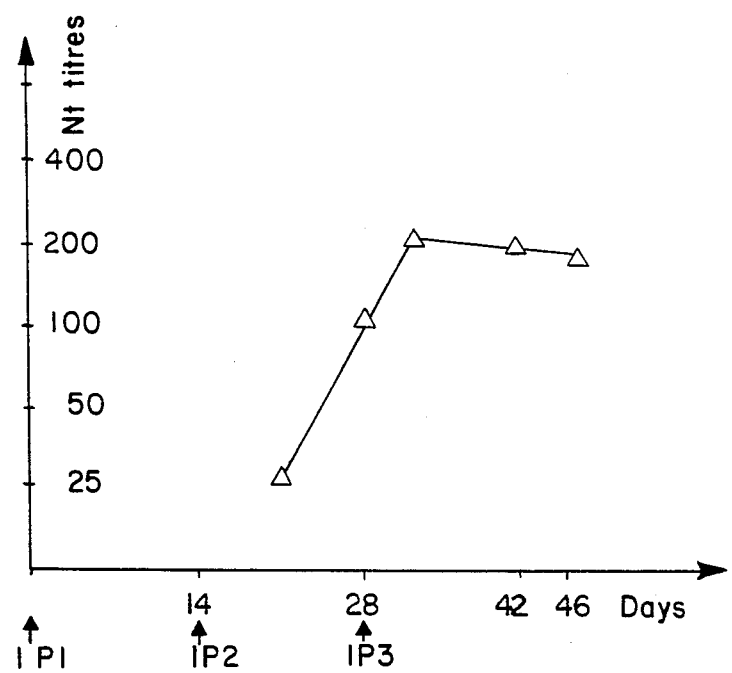

The present invention is based upon the surprising discovery that whole viruses, viral antigens and fragments thereof in which the structure of an oligosaccharide moiety of a viral glycoprotein has been "perturbed" are recognized more efficiently by serum, plasma or immunoglobulin fractions containing neutralizing antibody molecules. As used throughout the instant specification, the terms "perturbed" oligosaccharide and oligosaccharide "perturbation" are intended to encompass a variety of different types of modifications such as a modification (1) that alters the chemical or physical structure of a naturally occurring carbohydrate residue; (2) that removes, wholly or in part, a naturally occurring carbohydrate residue; and/or (3) that prevents or alters the addition of a carbohydrate residue to a virus, viral antigen of fragment thereof. Any techniques known in the art for achieving such oligosaccharide "perturbations" including, but not limited to chemical and enzymatic treatment and genetic engineering methods, are intended to fall within the scope of the present invention.

Based on this discovery, one embodiment of the present invention provides a novel method for detecting, as well as quantitating, the presence of virus neutralizing antibodies in samples of body fluids such as serum, plasma, various immunoglobulin fractions, etc. The novel method of the invention has the following advantages over conventional assays for neutralizing antibodies: (1) does not require use of cell culture techniques; (2) does not require use of injectious virus; (3) comprises a straight-forward serological assay; and (4) is complete in 4 hours or less. In contrast, conventional assays for virus neutralizing antibodies require: (1) cells in culture; (2) infectious virus; (3) skilled personnel; and (4) 5 days or so before an answer can be obtained. Thus, the present method is faster, easier and less complex than conventional methods. It does not require skilled personnel trained in the handling of infectious viral materials and is safer for use because even trained personnel need not be exposed to infectious virus.

Another embodiment of the present invention provides a novel method for preparing compositions comprising a virus, viral antigen or fragment thereof in which the oligosaccharide moiety is perturbed such that the compositions are useful for eliciting the formation of neutralizing antibodies which are capable of affording a protective immune response. Thus these compositions provide vaccine formulations which stimulate an active immune response for prophylaxis of viral infections. For example, according to this embodiment a viral antigen is prepared having a perturbed oligosaccharide moiety and administered as a vaccine formulation to actively elicit the production of protective antibodies.

Another alternate embodiment of the present invention provides a variety of novel methods for preparing or identifying monoclonal or polyclonal neutralizing antibodies which can be administered to confer short-term passive immunity for prophylaxis and/or therapy of viral infections. For example, a perturbed viral antigen is used to identify those monoclonal antibodies prepared by hybridoma techniques which are capable of neutralizing virus and which are capable of affording a protective immune response. Such antibodies could be administered for prophylactic treatment of persons at risk of developing a particular viral disease.

4. BRIEF DESCRIPTION OF THE FIGURES

The present invention may be more fully understood by reference to the following detailed description, examples of specific embodiments and the appended figures in which FIG. 1 (A–D) are graphs which illustrate the formation of antibodies following in vivo administration of untreated parainfluenza virus (PIV) virus (A; control); PIV having an oxidized oligosaccharide moiety (B); PIV conventionally inactivated using beta-propiolactone (C); and PIV conventionally inactivated using beta-propiolactone and having an oxidized oligosaccharide moiety (D). Antibody titers were evaluated following 2 intraperitoneal injections of each of the PIV preparations. Antibody titers in sera were assessed using: an oxidized oligosaccharide ELISA according to the invention ( — ); a conventional neutralization assay (Δ—Δ); an a conventional adsorption ELISA assay ( — ).

FIG. 2 (A—B) are graphs illustrating persistence of neutralizing antibody in sera of mice following intraperitoneal administration of PIV having an oxidized oligosaccharide moiety.

5. DETAILED DESCRIPTION OF THE INVENTION

The present invention relates to novel methods for diagnosis, prognosis, prophylaxis and therapy useful for a variety of viral infections. All the novel methods are based upon utilization of either whole virus, viral antigens or fragments of viral proteins in which "perturbation" of an oligosaccharide moiety renders the virus, viral antigen or fragment thereof more efficiently recognizable by neutralizing antibodies.

5.1. OLIGOSACCHARIDE PERTURBATIONS

According to the present invention, oligosaccharide "perturbation" encompasses a variety of modifications such as a modification (1) that alters the chemical or physical structure of a naturally occurring carbohydrate residue; (2) that removes, wholly or in part a naturally occurring carbohydrate residue; and/or (3) that prevents or alters the addition of a carbohydrate residue to a virus, viral antigen or fragment thereof. Illustrative examples of oligosaccharide perturbations include, but are not limited to the following.

Whole viruses, viral antigens or fragments thereof are perturbed by mild oxidation of an oligosaccharide moiety of a viral glycoprotein. For example, chemical oxidation of the oligosaccharide moiety can be accomplished using a variety of oxidizing agents such as periodic acid, paraperiodic acid, sodium metaperiodate, and potassium metaperiodate. Oxidation using such oxidizing agents is carried out by known methods. For a general discussion, see Jackson, in Organic Reactions 2, p. 341 (1944); Bunton, in Oxidation Chemistry, Vol. 1., Wiberg, ed., p. 367, Academic Press, New York (1944). The amount of the oxidizing agent depends on the kind of virus or viral antigen, but generally is used in excess of the amount of oxidizable oligosaccharide. The optimal amount can be determined by routine experimentation. The optimal ranges include: pH from about 4 to 8, a temperature range of about 0° to 37° C., and a reaction period of from about 15 minutes to 12 hours. During oxidation, light is preferably excluded from the reaction mixture in order to prevent over oxidation. Alternatively oxidation is achieved using an enzyme, such as galactose oxidase [Cooper et al., J. Biol. Chem. 234: 445-48 (1959)]. The influence of pH, substrate concentration, buffers and buffer concentration on the enzymatic oxidation are reported in Cooper et al., supra.

Whole viruses, viral antigens, or fragments thereof are perturbed by culturing virus infected cells in the presence of glycosylation inhibitors. For example, infected cells may be cultured in the presence of glycosylation inhibitors including, but not limited to: tunicamycin, streptoviridins, and/or glycosidase inhibitors such as carbohydrate analogs such as 2-deoxy-D-glucose and the like, and castanospermine, norjirimycin, 1-deoxynorjirimycin, bromocenduritol, 1-deoxymannojirimycin, and swainsonine, etc.

Whole viruses, viral antigens or fragments thereof are perturbed by enzymatically removing, either wholly or in part, a naturally occurring oligosaccharide moiety by exposing either virus infected cells in culture or isolated virus particles or fragments thereof to an enzyme which is specific for glycoside residues. Useful enzymes include neuraminidase, endo-beta-N-acetyglucosaminidases and the like.

Perturbation of viral antigens according to the present invention is also accomplished using genetic engineering techniques. For example, a gene encoding a particular viral glycoprotein or fragment may be cloned and expressed in a bacterial organism. In such case, little to no glycosylation of the expressed viral protein occurs, resulting in a perturbed oligosaccharide. Alternatively, a gene encoding the desired viral glycoprotein or fragment can be cloned and expressed in a eukaryotic organism or cell culture. The eukaryotic organism or cell is then cultured in the presence of a glycosylation inhibitor such as tunicamycin or a glycosidase inhibitor such as castanospermine, norjirimycin, and the like resulting in expression of a protein or fragment having a perturbed oligosaccharide. Yet another alternative is to use site-selective mutagenesis techniques to alter a gene encoding a viral antigen or fragment in such a way as to remove or change the site(s) of glycosylation.

In cases where the amino acid sequence of a viral glycoprotein or fragment is known, chemical methods of peptide synthesis provide yet another method for the preparation of a viral antigen or fragment thereof with a perturbed oligosaccharide.

The foregoing are merely illustrative examples of methods of oligosaccharide perturbation. Any other techniques known to those of skill in the art are intended to be encompassed by the perturbed oligosaccharide moiety.

The perturbed oligosaccharide of the virus, viral antigen or fragment thereof may be further modified, for example, by reduction with reducing agents such as sodium borohydride, cyanoborohydride and the like or by covalent attachment to a soluble or insoluble carrier or support.

5.2. APPLICATIONS

The viruses, viral antigens and fragments thereof according to the present invention are advantageously used for methods suited for a number of different applications.

5.2.1. DIAGNOSTIC AND PROGNOSTIC APPLICATIONS

According to one embodiment of the invention, the virus, viral antigen or fragment thereof having a perturbed oligosaccharide moiety is used in a variety of methods for assaying a sample of body fluids such as serum, plasma, cerebrospinal fluid, milk or partially purified immuno-globulin fractions or ascites fluid or supernatant produced by hybridoma cell lines or transformed cell lines which produce virus-specific antibody for the presence and titer of neutralizing antibodies.

The viruses, viral antigens or fragments thereof are used as ligands (antigens) to detect the presence of virus neutralizing antibodies in assay systems including but not limited to systems such as: Enzyme-Linked Immunosorbent Assays (ELISA), radioimmunoassays (RIA), immunofluoresence or other fluorescence-based assays, agglutination assays, etc. Examples of viruses for which neutralizing antibody titers are assayed would include those such as described in Section 4.3.

The titers obtained using assays with conventionally treated viruses, for example, conventional ELISA assays, which measure all antibodies, whether neutralizing or non-neutralizing, do not correlate with the titer determined in conventional virus neutralization assays.

On the other hand, the titers obtained using the present viruses, viral antigens or fragments thereof having a perturbed oligosaccharide moiety (hereinafter referred to as a "perturbed antigen") have been found by Applicants to be significantly correlated with the titer of virus neutralizing antibodies, as determined by conventional virus neutralization assays. (See, for example experimental results presented in Sections 5-7, infra). This may be due to a decrease in the binding of non-neutralizing antibody. Hence assays utilizing the present perturbed antigens are useful for diagnostic and/or prognostic prediction of the immuno-competent status of a patient with respect to a particular virus.

The method of the invention for detecting virus neutralizing antibodies in an aqueous sample comprises:

(a) contacting a ligand which comprises a virus, viral antigen or fragment thereof having a perturbed oligosaccharide moiety with an aqueous sample suspected of containing virus neutralizing antibodies in an assay system selected from the group consisting of an enzyme-linked immunosorbent assay, a radioimmunoassay, an agglutination assay, and an immunofluorescence assay and the like; and (b) detecting any reaction with the ligand; in which any reaction with the ligand indicates the presence of neutralizing antibodies in the sample. When quantitating the virus neutralizing antibodies is desired the method further comprises: comparing any reaction of ligand and antibodies to that of a standard.

5.2.1.1. DISSOCIATION AND REASSOCIATION OF IMMUNE COMPLEXES

In certain instances, for example, during an ongoing viral infection, virus or virus fragments may be present in varying amounts in serum or plasma samples. These virus or virus fragments could be bound or associated with neutralizing and non-neutralizing antibodies in immune complexes. Consequently, the titer obtained using the present perturbed antigens in in vitro assays may be artifically high. Hence, according to a further improved embodiment of the present invention, such immune complexes are dissociated prior to performing diagnostic assays to separate sera having immune complexes from those not having immune complexes. Dissociation of immune complexes can be accomplished by methods known to those of skill in the art including but not limited to: use of chaotropic agents such as perchlorate ($ClO_4^-$), thiocyanate ($SCN^-$), etc., denaturing agents such as guanidine hydrochloride, urea, etc. and use of variation of pH, and the like. After dissociation, the liberated antibodies are contacted with perturbed antigens according to the present invention under conditions which permit association or reassociation with neutralizing antibodies.

According to yet another embodiment of the invention, dissociation-reassociation of immune complexes present in aqueous samples of body fluids may be used to detect and/or quantitate the presence not only of neutralizing antibodies, but also of antibodies specific to antigens associated with the pathogenesis of autoimmune diseases which may be bound or associated with such antibodies in immune complexes. Thus according to this embodiment of the invention, antibodies present in immune complexes in an aqueous sample are detected by: (1) dissociating any immune complexes which are present in the aqueous sample; (2) contacting the dissociated complexes with a ligand which comprises an antigen associated with pathogenesis of an auto-immune disease in an assay selected from the group consisting of an enzyme-linked immunosorbent assay a radioimmunoassay, an agglutination assay and an immunofluorescence assay; and (3) detecting any reaction with the ligand, in which any reaction indicates the presence of antibody in the sample. Alternatively, antigens in immune complexes in aqueous samples may be detected by: (1) dissociating any immune complexes which are present in the aqueous sample; (2) contacting the dissociated complexes with a ligand which comprises an antibody specific for an antigen associated with pathogenesis of an auto-immune disease in an assay selected from the group consisting of an enzyme-linked immunosorbent assay a radioimmunoassay, an agglutination assay and an immunofluorescence assay; and (3) detecting any reaction with the ligand, in which any reaction indicates the presence of antigen in the sample.

5.2.2. PROPHYLACTIC AND THERAPEUTIC APPLICATIONS

According to another embodiment of the present invention, the viruses, viral antigens and fragments thereof having a perturbed oligosaccharide moiety obtained either by chemical or enzymatic oxidation methods described in section 5.1 are used as immunogens in vaccine formulations to stimulate an active, protective immune response in a vaccinated host.

When a whole virus having an oxidized oligosaccharide moiety is used, it is necessary to use either an attenuated or avirulent virus or an inactivated virus. An inactivated virus is obtained by treatment of a virus with various chemicals such as formaldehyde; then an oligosaccharide is perturbed using any of the methods described above in Section 5.1. Alternatively, an inactivated virus having an oxidixed oligosaccharide moiety is obtained by chemical oxidation of a virus, for example, using periodic acid as described in Section 5.1. Such attenuated or inactivated viruses having an oxidized oligosaccharide moiety induce antibodies that are more effective at neutralizing viral infections than conventionally attenuated or inactivated viruses.

Subunit vaccines containing only the necessary and relevant immunogenic material such as capsid glycoproteins of non-enveloped icosohedral viruses or the peplomers (glycoprotein spikes) of enveloped viruses or immunogenic fragments thereof can also be prepared in which the oligosaccharide moiety of the glycoprotein or fragment thereof is perturbed according to the present invention. Subunit vaccines can be prepared by isolating the relevant subunit from highly purified viral fractions or using recombinant DNA technology and perturbing the oligosaccharide moiety of the relevant immunogenic subunit as described in Section 5.1.

The vaccine formulations which stimulate an active immune response for prophylaxis of viral infections can be prepared by mixing the virus, viral antigen or fragment thereof having a perturbed oligosaccharide moiety in a carrier suitable for use in vivo. In order to enhance the immunological response of the host, the immunogenic virus, antigen or fragment thereof may be formulated with a suitable adjuvant. Suitable adjuvants include, but are not limited to: aluminum hydroxide, surface active substances, lysolecithin, pluronic polyols, polyanions, peptides including but not limited to muramyl peptides, and oil emulsions.

According to another alternate embodiment, a vaccine formulation to stimulate an active immune response for prophylaxis of viral infections is prepared by coupling a virus, viral antigen or fragment thereof having a perturbed oligosaccharide moiety to an immunogenic peptide or compound in order to enhance or potentiate the immunological response of the host.

According to yet another embodiment, the vaccine formulation can be prepared as a multivalent vaccine. To this end, a mixture of different viruses, viral antigens or fragments thereof each of which contains a perturbed oligosaccharide moiety and which is capable of eliciting an immune response against a different viral pathogen can be mixed together in one formulation.

Many methods can be used to introduce the vaccine formulations described above into a host. These include, but are not limited to: intradermal, intramuscular, intraperitoneal, intravenous, subcutaneous, and intranasal routes of administration.

According to another embodiment of the present invention, the viruses, viral antigens and fragments thereof having a perturbed oligosaccharide moiety are used in a variety of methods to prepare neutralizing antibodies which can be administered to confer short-term passive immunity for prophylaxis and/or therapy of viral infections. In one mode of this embodiment, a virus, viral antigen or fragment thereof having a perturbed oligosaccharide moiety is used as an immunogen in any technique that provides for the production of antibody molecules by continuous cell lines in culture. For example, the present immunogens can be utilized in the hybridoma methods originally developed by Kohler and Milstein, and reviewed by them in Sci. Amer. 243: 66–74 (1980) as well as in the human B-cell hybridoma methods described by Kozbor et al., Immunology Today 4: 72 (1983) and the EBV-hybridoma methods for producing human monoclonal antibodies described by Cole et al., in Monoclonal Antibodies and Cancer Therapy, Alan R. Liss, Inc., pp. 77–96 (1985) and the like. The monoclonal antibodies produced provide a readily available, consistent source of neutralizing antibodies specific for relevant virus which can be administered for passive immunization.

This embodiment of the invention encompasses a method for preparing a composition for administration to an animal or a human to confer short-term passive immunity or for prophylaxis or therapy of a viral-induced infection comprising: harvesting monoclonal antibodies produced by a hybridoma cell line formed by fusing a myeloma or hybridoma cell and a cell capable of producing antibody against a virus, viral antigen or fragment thereof having a perturbed oligosaccharide moiety. It further encompasses a method for preparing a composition for administration to an animal or a human to confer short-term passive immunity or for prophylaxis or therapy of a viral-induced infection comprising: harvesting monoclonal antibodies produced by a lymphocyte cell line formed by transformation by an EBV virus of a mammalian lymphocyte cell capable of producing antibody against a virus, viral antigen or fragment thereof having a perturbed oligosaccharide moiety. Additionally it encompasses a method for preparing a composition for administration to an animal or a human to confer short-term passive immunity or for prophylaxis or therapy of a viral-induced infection comprising: (a) contacting a sample containing anti-viral antibodies with an antigen comprising a virus, viral antigen or fragment thereof having a perturbed oligosaccharide moiety to form an antibody-antigen complex; (b) separating the antibody-antigen complex from the sample; and (c) dissociating the antibody-antigen complex to obtain a purified antiviral antibody composition.

In another mode of this embodiment, a virus, viral antigen or fragment thereof having a perturbed oligosaccharide moiety is used in a screening assay to identify those viral-specific monoclonal antibodies which although known in the art have not been recognized as neutralizing antibodies. Hence this method screens for and identifies neutralizing monoclonal antibodies which can then be administered for passive immunization.

In yet another alternative mode of this embodiment of the present invention, a virus, viral antigen or fragment thereof is used to prepare neutralizing antibodies from serum, plasma or fractions of immunoglobulins derived therefrom. For example, a virus, viral antigen or fragment having a perturbed oligosaccharide moiety is immobilized and used in a preparative affinity chromatography format to isolate relevant neutralizing antibodies from serum or plasma by the formation of immune complexes. The polyclonal neutralizing antibodies are then separated from the immune complexes by conventional techniques.

The neutralizing antibodies which react specifically with the compositions of the present invention containing a perturbed oligosaccharide moiety can be formulated to confer short-term passive immunity to the host. Adjuvants are not needed in this type of preparation because the object is not to stimulate an immune response, but rather to inactivate or bind a viral pathogen. Thus, any suitable pharmaceutical carrier can be used. Passive immunization using such preparations can be utilized on an emergency basis for immediate protection of unimmunized individuals exposed to special risks of viral infections. Additionally, such preparations can be used prophylactically for viral infections such as measles and hepatitis.

In its most general form, the method of this embodiment of the invention encompasses a method for protection of an animal or a human from an infection induced by a virus, comprising: administering to an animal or human an effective amount of a vaccine formulation which comprises a virus, viral antigen or fragment thereof having a perturbed oligosaccharide moiety.

Such formulations can be administered to a host by routes including but not limited to: intradermal, intramuscular, intraperitoneal, intravenous and subcutaneous.

5 3. VIRUSES AND VIRAL ANTIGENS

The viruses, viral antigens and fragments thereof which are intended to be encompassed by the present invention include a wide variety of viruses such as DNA and RNA viruses including but not limited to retroviruses.

Specific examples include: DNA viruses such as: Adenoviridae such as adenoviruses subgroups B, C, D, E, F and G, etc; Herpesviridae such as herpes simplex I and II, cytomegalovirus, Epstein-Barr virus, varicella-zoster, etc.; Orthomyxoviridae such as influenza viruses, etc; Hepadnaviridae such as hepatitis B, hepatitis non-A, non-B, etc.; Parvoviridae such as parvoviruses, etc.; RNA viruses such as Togaviridae such as rubella, etc.; Paramyxoviridae such as measles, parainfluenza, respiratory syncytial virus, etc.; Flaviviridae such as dengue virus types 1–4, yellow fever virus, tick-borne fever viruses, etc.; Rhabdoviridae such as rabies, vesicular stomatitis virus, Marburg-Ebola virus, etc.; Bunyaviridae such as Rift Valley Fever, California encephalitis virus group, sand fly fever virus, etc.; Arenaviridae such as Lassa fever virus, Junin virus, lymphocytic choriomeningitis virus, etc.; Reoviridae such as rotovirus, etc.; Picornaviridae such, as polio virus, coxsackieviruses, hepatitis A virus, rhinovirus, etc.; Retroviridae such as human lymphoadenopathy-associated virus (LAV, HIV, HTLV-III), human T-cell lymphotrophic virus types I, II, III, feline leukemia virus, etc.

The following Examples are given for the purpose of illustration and not by way of limitation on the scope of the invention.

In the ELISA assays described below in which the virus was covalently attached to the microtiter plate, the microtiter plates were pre-saturated using either 200 ul of 0.5% calf IgG in 0.14 M NaCl or 300 ul of 0.5% bovine serum albumin in 0.5 M Tris-citrate buffer containing 0.1% Tween-20, 20 pH 8.1 in order to eliminate the non-specific adsorption of virus or serum proteins or IgG. In the ELISA assays described below in which the virus was attached to the plate via adsorption, the virus was allowed to adsorb to the plate and then the plates were saturated using either calf IgG in 0.14 M NaCl or bovine serum albumin in 0.5 M Tris-citrate buffer.

6. EXAMPLES: DETERMINATION OF NEUTRALIZING ANTIBODIES IN PURIFIED HUMAN IgG FROM SERA

6.1. DETECTION OF NEUTRALIZING ANTI-CMV ANTIBODIES IN HUMAN IgG

The following series of experiments demonstrate that ELISA assays in which the oligosaccharide moiety of the viral antigen was perturbed according to the present invention are useful for determining the titer of virus-neutralizing antibodies. In contrast, conventional ELISA assays in which the virus was either adsorbed or covalently attached without perturbation of the oligosaccharide moiety are not.

The antigen used in the assays was whole cytomegalovirus (CMV) obtained from homogenates of cultured human fibroblast cells ($MRC_5$) infected with CMV for six to eight days. The microtiter wells containing an equivalent amount (about 1 ug/well) of CMV were prepared for the various ELISA assays as follows:

(A) ELISA'S Using Antigen With Perturbed Oligosaccharide.

(1) Virus Covalently Attached Via Oxidized Oligosaccharide Moiety

The carbohydrate moiety of CMV was oxidized using sodium periodate ($NaIO_4$) as described in Section 5 and covalently coupled to a reactive amine on a side chain of the polyhydrazidostyrene of the well. Addition of a reactive amine group to polystyrene (or the microtiter well) was carried out by the method of Chin and Lanks [Anal. Biochem, 83: 709-19 (1977)]. Polystyrene was first converted to nitrostyrene which was then reduced to aminostyrene. Polyaminostyrene was then converted to polyhydrazidostyrene in a two-step process: (1) polyaminostyrene was succinylated; and then (2) an amide bond was formed betwen hydrazine and the succinylated polyaminostyrene using carbodiimide. (0x Oligosaccharide Attached ELISA).

(2) Virus Covalently Attached Via Amine Group, Oxidized Oligosaccharide Moiety

The CMV virus was covalently attached to the polycarbostyrene via a peptide bond formed using carbodiimide to couple an amine residue of the virus to an activated carboxyl of the polycarbostyrene. The carbohydrate moiety of the virus was then oxidized in situ using $NaIO_4$ as described in Section 4. (Amine Attached Oligosaccharide Ox ELISA).

(B) Conventional ELISA'S Using Antigen with Non-Perturbed Oligosaccharide.

(1) Virus Covalently Attached Via Amine Group

CMV was attached using carbodiimide to form a peptide bond between an amine group of an amino acid residue of the virus and a free carboxyl group of a polycarbostyrene of the well. (Amine Attached ELISA).

(2) Virus Non-Covalently Attached

CMV was simply non-covalently fixed by adsorption onto a non-modified polystyrene well. (Adsorption ELISA).

Partially purified human IgG was obtained from human serum samples using conventional ammonium sulfate precipitation techniques. After precipitation, the tubes were centrifuged at 12,000 rpm for 5 minutes. The supernatant was discarded, the pellet was washed, recentrifuged and resuspended in 0.14 M NaCl. The partially purified human IgG samples were serially diluted in Buffer I of the following composition:

| | |
|---|---|
| Calf IgG | 0.5% |
| NaCl | 0.14 M |
| Glycine | 0.1 M |
| Sodium borate | 0.05 M |
| Synperonic PE/L62 | 0.10% (v/v), | adjusted to pH 8.1 with 1.0 M HCl. 100 ul of each dilution was distributed in the wells of the plate containing the CMV. After two hours incubation at 37° C., the plates were washed in the Buffer I, but without calf IgG.

Then 100 ul of a goat serum solution containing anti-human IgG labeled with alkaline phosphatase, diluted to 1/1000 in the following Buffer II, was introduced into each well:

| | |
|---|---|
| Bovine serum albumin | 1.0% |
| NaCl | 0.14 M |
| Glycine | 0.1 M |
| Borate | 0.05 M |
| Synperonic PE/L62 | 0.10% (v/v) |

After a contact time of one hour at 37° C., the wells were washed with Buffer II but without bovine serum albumin (BSA). The enzymatic activity was determined at 37° C. using p-nitrophenyl phosphate as substrate at a concentration of 0.2% (p/v) dissolved in a buffer containing: 2-amino-2-methyl-1-propanol (0.625 M) and $MgCl_2$ (2.0 mM), pH 10.25. The optical density was measured at 405 nm either every five minutes during a period of 30 minutes or after 30 minutes of incubation.

A conventional CMV infective power neutralization assay was performed using $MRC_5$ cells in culture as described by Krech et al., Z. Immun.-Forsch, Bd. 141S: 411-29 (1971).

Results are illustrated in Table 1. The antibody titer obtained using the ELISA assays and the conventional virus neutralization assays were calculated as a protein concentration of 1 mg/ml of non-diluted IgG sample.

Table 2 presents the linear correlation coefficients obtained when the titers obtained by the various assays were compared.

TABLE 1
TITERS OF CMV-NEUTRALIZING ANTIBODIES IN PURIFIED IgG

| IgG Sample | Neutralization Titer | Ox Oligosaccharide Attached ELISA Titer | Amine Attached Oligosaccharide Ox ELISA Titer | Amine Attached ELISA Titer | Adsorption ELISA Titer |
|---|---|---|---|---|---|
| 1 | 128 | 50 | <50 | 400 | 67 |
| 2 | 256 | 50 | <50 | 200 | 144 |
| 3 | 256 | 100 | 100 | 400 | 519 |
| 4 | 512 | 400 | 100 | 800 | 1087 |
| 5 | 64 | <50 | <50 | 50 | 54 |
| 6 | 128 | 50 | 50 | 200 | 67 |
| 7 | 256 | 200 | 200 | 800 | 432 |
| 8 | 465 | 364 | 181 | 727 | 2780 |
| 9 | 621 | 485 | 485 | 485 | 1005 |
| 10 | 512 | 400 | 400 | >1600 | 2923 |
| 11 | 128 | 200 | 100 | 400 | 387 |
| 12 | 256 | 100 | 100 | 1600 | 593 |
| 13 | 64 | <50 | 50 | 54 | 100 |
| 14 | 256 | 50 | 50 | 455 | 400 |

TABLE 2
COMPARISONS OF ASSAYS FOR CMV-NEUTRALIZING ANTIBODIES

Linear Correlation Coefficients

| Assay | Neutralization | Adsorption ELISA Attached | Ox Oligosaccharide ELISA | Amine Attached ELISA | Amine Attached Oligo saccharide Ox ELISA |
|---|---|---|---|---|---|
| Neutralization | 1 | | | | |
| Adsorption ELISA | 0.74 | 1 | | | |
| Ox Oligosaccharide Attached ELISA | 0.90 | 0.75 | 1 | | |
| Amine Attached ELISA | 0.52 | 0.62 | 0.41 | 1 | |
| Amine Attached Oligosaccharide Ox ELISA[a] | 0.78 (0.87) | 0.65 (0.64) | 0.82 (0.93) | 0.46 (0.48) | 1 |

[a]The number in parentheses represents the correlation coefficient obtained when one aberrant titer value is discarded.

As demonstrated in Tables 1 and 2, the titer obtained using ELISA assays according to the present invention, i.e., the Ox Oligosaccharide Attached ELISA and the Amine Attached oligosaccharide Ox ELISA was highly positively correlated with the titer obtained using the conventional Neutralization Assay (correlation coefficients, respectively: 0.90 and 0.87). On the other hand, the titer obtained using the conventional Amine Attached ELISA showed no significant correlation with the titer of neutralizing antibody (correlation coefficient: 0.52). The Amine Attached ELISA showed much weaker, non-significant correlation with titer of neutralizing antibody (correlation coefficient: 0.74).

Table 2 demonstrates further that there was a significant positive correlation between the titer obtained using the Ox Oligosaccharide Attached ELISA and the Amine Attached Oligosaccharide Ox ELISA (correlation coefficient: 0.93). At the same time, however, there was no significant correlation observed between the titers obtained using the Adsorption ELISA and the Amine Attached Oligosaccharide Ox ELISA, or the Amine Attached Oligosaccharide Ox ELISA and the Amine Attached ELISA. This indicates that the significant correlation observed between the titers of neutralizing antibody using the Neutralization Assay and both the Amine Attached Oligosaccharide Ox ELISA and the Ox Oligosaccharide Attached ELISA is not related to the method of covalent attachment, but rather may be related to the perturbation of the oligosaccharide moiety achieved by oxidation. Moreover, these results suggest further that it does not matter whether the oligosaccharide perturbation occurs prior to or following covalent attachment of the virus to the microtiter well.

6.2. REPRODUCIBILITY OF NEUTRALIZING ANTIBODY TITER

The following experiment demonstrates the reproducibility of results obtained using an ELISA assay in which the virus was covalently attached to a insoluble support via an oxidized carbohydrate moiety of the virus.

A series of ELISA assays to determine the titer of neutralizing anti-CMV antibodies was performed as described in Section 6.1 in which CMV was covalently attached to a reactive amine on a side chain of an insoluble support via an oxidized carbohydrate moiety of the CMV antigen. The samples used were purified IgG obtained from the same serum samples used for the experiments described in Section 6.1. One set of ELISA's were performed on one aliquot of purified IgG's, and a duplicate set of assays were performed on another aliquot of the same IgG's some 17½ months later. The samples were stored frozen at −70° C. during the interim. Results are presented in Table 3.

TABLE 3
REPRODUCIBILITY OF CMV NEUTRALIZING ANTIBODY ASSAY

Antibody Titer - ELISA Virus Covalently Attached Via Oxidized Oligosaccharide

| Sample No. | Experiment 1 | Experiment 2 |
|---|---|---|
| 1 | 50 | 40 |
| 2 | 50 | 40 |
| 3 | 100 | 160 |
| 4 | 400 | 320 |
| 5 | <50 | 160 |
| 6 | 50 | 40 |
| 7 | 200 | 160 |
| 8 | 364 | 290 |
| 9 | 485 | 388 |
| 10 | 400 | 640 |
| 11 | 200 | 160 |

TABLE 3-continued
REPRODUCIBILITY OF CMV NEUTRALIZING ANTIBODY ASSAY

| Sample No. | Antibody Titer - ELISA Virus Covalently Attached Via Oxidized Oligosaccharide | |
|---|---|---|
| | Experiment 1 | Experiment 2 |
| 12 | 100 | 80 |
| 13 | <50 | 80 |
| 14 | 50 | 80 |

As demonstrated in Table 3, the results of antibody titers obtained using the ELISA assay in which the virus was covalently attached via a perturbed oligosaccharide moiety are highly reproducible.

7. EXAMPLE: DETECTION OF NEUTRALIZING ANTIBODIES IN SERUM SAMPLES

The following series of assays demonstrate that an ELISA assay in which the oligosaccharide moiety of a virus antigen was perturbed is useful for determining the titer of neutralizing antibody in human serum samples.

An ELISA assay was performed as described in Section 6.1 in which the oligosaccharide moiety of the CMV virus was oxidized and covalently coupled to a hydrazido group on the polyhydrazidostyrene of the microtiter well. A conventional ELISA assay was performed as described in Section 6.1 in which the CMV was merely adsorbed to the microtiter well. A virus neutralization assay as described in Section 6.1 was also performed.

Results of all three assays are compared in Table 4.

TABLE 4

| Serum Sample No. | Adsorption ELISA Titer[a] | Neutralization Assay Titer | Oxidized Oligosaccharide Attached ELISA Titer[b] |
|---|---|---|---|
| 1 | 6400 | 160 | 125 |
| 2 | 26600 | 320 | 250 |
| 3 | 102400 | 640 | 2000 |
| 4 | 25600 | 640 | 1000 |
| 5 | 102400 | 2560 | 4000 |
| 6 | 25600 | 2560 | 4000 |

[a]Correlation coefficient between Neutralization Assay Titer and Adsorption ELISA Titer: +0.37.
[b]Correlation coefficient between Neutralization Assay Titer and Oxidized Oligosaccharide Attached ELISA Titer: +0.96.

As demonstrated in Table 4, there was a highly significant positive correlation between the titer of antibodies in human serum samples measured by the Neutralization Assay and by an ELISA assay in which the oligosaccharide moiety of CMV was oxidized and covalently coupled to the microtiter well Thus using polyclonal sera, this ELISA assay is "predictive" of the immunocompetent status of the patient. In contrast, no correlation was observed between the antibody titer measured by the Neutralization Assay and that obtained using a conventional ELISA in which non-perturbed CMV virus was merely adsorbed to the microtiter well

8. EXAMPLE: PERTURBATION OF OLIGOSACCHARIDE MOIETY OF VIRUS AND ATTACHMENT OF VIRUS TO A SOLID SUPPORT

As suggested by results presented in Section 6.1 above, when a perturbed antigen is used to determine the titer of neutralizing antibodies in an ELISA format in which the antigen is covalently attached to the microtiter well, it does not matter whether the oligosaccharide moiety is perturbed before or after covalent attachment to the microtiter well. The following series of experiments was performed to investigate the effect of perturbation of the oligosaccharide moiety according to the present invention upon the ability of the virus to attach to a microtiter plate.

The oligosaccharide moiety of CMV virus was perturbed by oxidization using $NaIO_4$ for 16 hours at 4° C. as described in Section 5. ELISA assays for anti-CMV antibodies were conducted as described in Section 6.1, in which: (1) CMV having a perturbed oligosaccharide moiety in PBS was adsorbed to a polystryene microtiter plate. (2) CMV having a perturbed oligosaccharide moiety was covalently coupled via the carbohydrate moiety to a reactive amine group of a polyhydrazidostyrene microtiter plate in the presence of phosphate buffer containing 0.1% Tween-20 (PBT). PBT was used to prevent non-covalent adsorption of CMV to the polyhydrazidostyrene plate. (3) Non-perturbed CMV in PBS was adsorbed to a polystyrene microtiter plate.

Results are illustrated in Table 5.

TABLE 5
COMPARISON OF ELISA TITERS OF CMV WITH PERTURBED AND NON-PERTURBED OLIGOSACCHARIDE

| IgG No. | Ox CMV Adsorbed in PBS[a] | Ox CMV Covalently in PBT[b] | Non-Ox CMV Adsorbed in PBS[a] |
|---|---|---|---|
| Y 287 | 4000 | 4000 | 8000 |
| Y1096 | 1000 | 1000 | 8000 |

[a]CMV either native or having a perturbed oligosaccharide moiety in PBS (phosphate buffer saline, pH 7.4) was immobilized by adsorption onto polystyrene microtiter plates.
[b]CMV having a perturbed oligosaccharide moiety in PBT (50 mM phosphate buffer, 0.1% Tween-20, pH 6.0) was covalently coupled to polyhydrazidostyrene of microtiter plates.

As demonstrated in Table 5, there was no difference in ELISA titers obtained in which a perturbed antigen was either covalently attached or merely adsorbed to the micro-titer well. When the perturbed CMV was incubated in the microtiter wells in the presence of PBT, the titer obtained was zero because the perturbed virus does not adsorb in the presence of Tween-20 (results not shown).

9. EXAMPLE: PROTECTIVE IMMUNE RESPONSE AFFORDED BY PARAINFLUENZA VIRUS HAVING PERTURBED OLIGOSACCHARIDE MOIETY

The following example demonstrates that in vivo administration of parainfluenza virus (PIV) having a perturbed oligosaccharide moiety according to the present invention not only elicited formation of neutralizing antibodies, but also protected mice against a subsequent challenge with live virus.

9.1. NON-INFECTIVITY OF PARAINFLUENZA HAVING A PERTURBED OLIGOSACCHARIDE MOEITY

Parainfluenza virus (PIV) type 1 Sendai was cultured in the allantoic cavity of 8 day old embryonated eggs. After 3 days, the allantoic fluid was collected and concentrated by ultracentrifugation and ultrafiltration. PIV was purified by 2 successive cycles of centrifugation at 100,000 × g for 4 hours on a linear sucrose gradient 20–60% (w/v). The yield and purity of virus were assayed by determination of hemagglutination activity, infectious titer, protein content and electrophoretic profile on polyacrylamide gel electrophoresis (PAGE).

Preliminary experiments were performed to investigate the infectivity of PIV having an oxidized oligosaccharide moiety. The carbohydrate moiety of the whole purified PIV virion was oxidized using $NaIO_4$ as described in Section 5.1. The reaction was stopped by the addition of sodium sulphite. The oxidized virus was dialysed extensively against PBS at 4° C. (3 changes).

Infectivity of PIV inactivated by a conventional method using beta-propiolactone was also determined for comparison. Beta-propiolactone (Fluka) was added (final concentration 0.05% v/v) to purified PIV (2 mg protein/ml) in 100 mM sodium borate-HCl, pH 9.0, and the mixture incubated for 2 hours 37° C. At that time, fresh beta-propiolactone was added (final concentration 0.05% v/v) and the mixture incubated for an additional 2 hours. The virus was then dialysed extensively against PBS at 4° C. (3 changes).

Another sample of purified PIV was first conventionally inactivated using beta-propiolactone and then the oligosaccharide moiety oxidized as described above. The inactivated oxidized PIV was then extensively dialysed against PBS at 4° C. (3 changes).

Untreated PIV, incubated for 4 hours in 100 mM sodium borate-HCl, pH 9.0, at 37° C. and then dialysed extensively against PBS, served as the control.

The yield of virus obtained following each of the above treatments was determined by estimation of the protein content following treatment. Yields were 50%, 75% and 52% of control respectively for oxidized, inactivated and inactivated-oxidized PIV. After adjusting all preparations to the same protein content, 50 ul aliquots of each were tested for infectivity as follows:

A 50 ul aliquot of a primary culture of Rhesus monkey kidney cells ($3 \times 10^5$ cells/ml) was seeded into 96 well Falcon micro-titer plates. Once the cells were attached, 50 ul of a series of 10-fold dilutions of the treated PIV samples were added to the wells (4 wells/dilution). The infectious titer of PIV represents the last dilution which still resulted in (a) characteristic cytopathic effects of PIV on the monkey kidney cells; and (b) typical hemadsorptic pattern using guinea pig red blood cells using an assay described in Vogel et al., Science 126:358–59 (1957) adapted for use in microtiter plate.

Results obtained are presented in Table 6.

TABLE 6

INFECTIVITY OF PARAINFLUENZA VIRUS (PIV)

| Sample No. | Infectious PIV Titer[a] Treatment | | | |
|---|---|---|---|---|
| | Control | Oligosaccharide Oxidation | Conventional Inactivation | Conventional Inactivation & Oxidation |
| 1 | $>10^9$ | <10 | <10 | <10 |
| 2 | $10^5$ | <10 | <10 | <10 |

[a]Infectious titer of dilutions of 50 ul of treated samples of PIV were obtained after adjusting all samples to the same protein content as described in the text. The titer represents the last dilution which still resulted in (a) characteristic cytopathic effects of PIV in cultured monkey cells; and (b) typical hemadsorption pattern using guinea pig red blood cells. See text for details.

As demonstrated in Table 6, oxidation of the oligosaccharide moiety of PIV effectively destroyed the infectivity of the virus. In fact, oxidation of the carbohydrate moiety of the PIV virion was as effective as conventional inactivation using beta-propiolactone.

9.2. INDUCEMENT OF NEUTRALIZING ANTIBODIES

The following experiment demonstrates that intraperitoneal administration of PIV having a perturbed oligosaccharide moiety effectively induced the formation of neutralizing antibodies in experimental animals.

Sixty-six 4 week old female CBA/JICO mice were divided into one group of six animals (control group) and 3 groups of 20 experimental animals (Series A, B, and C). Animals in each Series were further subdivided into four treatment groups: Group 1 (control) untreated PIV; Group 2, PIV having an oxidized oligosaccharide moiety; Group 3, PIV conventionally inactivated using beta-propiolactone; and Group 4, PIV conventionally inactivated using beta-propiolactone and having an oxidized oligosaccharide moiety. Animals in Series A, Series B and Series C received respectively-one (on day 0) two (on days 0 and 14) and 3 (on days 0, 14 and 28) intraperitoneal injections of the appropriate PIV preparations (70 ug PIV in 100 ul PBS and 100 ul Fruend's complete adjuvant).

Serum samples were obtained from animals via retroorbital puncture 14 days after the last injection of PIV preparations for each Series. Antibody titer of the serum samples was evaluated using three different assays as follows:

(1) Oxidized Oligosaccharide Attached ELISA. An ELISA assay was performed as described in Section 6.1. in which the antigen used comprised PIV having an oxidized oligosaccharide moiety covalently coupled to a hydrazido group on the polyhydrazido styrene of the microtiter well.

(2) Conventional Adsorption ELISA. A conventional ELISA assay was performed in which the PIV was fixed merely by adsorption onto the non-modified polystyrene microtiter well. Briefly, 0.1 ug purified PIV in PBS, pH 7.2, was allowed to adsorb onto the wells by incubation for 16 hours at room temperature. The wells were then washed with PBS containing 0.05% Tween 20 (PBT-0.05).

Serum samples, diluted in PBT-0.05 100 ul were distributed in the wells of the plates containing PIV. The sence and titer of anti-PIV antibody was determined as described in Section 6.1. using goat anti-mouse IgG labeled with alkaline phosphatase.

(3) Conventional PIV Neutralization Assay. A virus neutralization assay was performed as follows: Serial 2-fold dilutions of serum were incubated for 1 hour at 37° C. in the presence of an equal volume of virus containing 30–100 times the dose of virus capable of producing a cytopathic effect on 50% of cells in tissue culture. ($TCID_{50}$) 100 ul of the mixture were then added to each well of Falcon microtiter plates containing 50 ul of a suspension of Rhesus monkey kidney cells at $3\times10^5$ cells/ml. Incubation was carried out at 30° C. in a humid atmosphere of air/$CO_2$ (95/5). The neutralizing titer of the serum represents the highest dilution which still inhibits the cytopathic effect of the virus.

Results obtained using all three assays are illustrated in FIG. 1 (A–D). As indicated in FIG. 1, antibody titer rose appreciately from day 18–32 in all animals which received PIV preparations as immunogen. In mice which received either untreated PIV or PIV having an oxidized oligosaccharide moiety as immunogen, the rise in neutralizing antibody titer at days and 28 followed the same pattern when assayed by the oxidized oligosaccharide attached assay and conventional neutralization assays (FIG. 1A, B). In mice which received conventionally inactivated virus, there was a lag in the neutralizing antibody titer (FIG. 1C). In mice which received PIV which was both conventionally inactivated and in which the oligosaccharide moiety was oxidized as immunogen, the titer of neutralizing antibody obtained using virus neutralization assay remained low.

From results presented in FIG. 1, it is clear that PIV having an oxidized oligosaccharide moeity is effective in eliciting a significant neutralizing antibody response when administered in vivo. This response occurred earlier than that elicited by PIV inactivated by conventional methods using beta-propiolactone.

In order to determine persistence of neutralizing antibody elicited by PIV having an oxidized oligosaccharide moiety, a series of experiments was performed in which animals received two-three intraperitoneal injections of the perturbed PIV as immunogen at day 0, 14 and 28. Serum samples were collected and the neutralizing antibody titers was assayed using biological neutralization test. Results obtained are illustrated in FIG. 2.

As demonstrated in FIG. 2, three intraperitoneal injections of oxidized PIV were necessary to maintain maximum neutralizing antibody titer for up to 42 days.

9.3. PROTECTIVE IMMUNE RESPONSE

The critical requirement for a successful vaccine formulation is the ability not only to induce neutralizing antibody, but more importantly, to elicit a protective immune response against infectious virus. The following experiment demonstrates that animals previously immunized using PIV having an oxidized oligosaccharide moeity were effectively protected against subsequent challenge with infectious PIV virus.

The same group of 66 female mice as described in Section 9.2 were used as experimental animals. An additional group of 12 mice which were not immunized served as controls. On the 14th day following the last intraperitoneal administration of the appropriate PIV preparation, all animals from Series A, B and C, were challenged intranasally with $10^3$ $TCID_{50}$ of untreated PIV. Control mice were similarly challenged. Four days following challenge with untreated (live) PIV, animals were sacrificed and the presence of infectious virus was evaluated in lung tissues as follows:

Lung tissues were homogenized in minimal essential medium (MEM) containing trypsin at a concentration of 5 ug/ml (MEM-trypsin). Aliquots of the lung homogenates were diluted in MEM-trypsin and added to culture tubes containing $1\times10^4$ MA $10_4$ cells (a cell line derived from Rhseus monkey kidney cells). After the cells were cultured for three days, the virus titer was determined by hemadsorption. Comparison of the titer obtained in pulmonary homogenates of non-immunized control animals permitted the degree of protection to be estimated.

In non-immunized mice, virus multiplication in the lungs resulted in a PIV titer of $1.5\times10^6$ $TCID_{50}$ in lung homogenates four days post-challenge. In contrast, in animals previously immunized with one intraperitoneal injection of PIV having an oxidized carbohydrate moiety, the titer of virus recovered was only $7.5\times10^2$ $TCID_{50}$. In animals immunized with either 2 or 3 intraperitoneal injections, no virus was detected in lungs, four days following challenge with infectious virus.

In animals which had been previously immunized with one, two or three intraperitoneal injections of either conventionally inactivated PIV or conventionally inactivated PIV having an oxidized carbohydrate moiety, no virus could be detected in lung homogenates at any time post-challenge with infectious virus. Thus it appears that PIV having an oxidized oligosaccharide moiety either with or without conventional inactivation is very effective in elicting a protective immune response against infectious PIV.

10. EXAMPLE: BIOLOGICAL ACTIVITY OF VIRUSES HAVING A PERTURBED OLIGOSACCHARIDE MOIETY

The following experiments demonstrate that oxidation of the carbohydrate moiety of influenza virus (an RNA virus) and of adenovirus (a DNA virus) is effective in destroying infectivity and/or hemagglutination ability of the virus.

The oligosaccharde moiety of influenza virus A Hong Kong 168 and of Adenovirus type 5 (AdV5) whole virions was oxidized according to the present invention as described in Section 5.1. The biological activity of the virions having oxidized carbohydrate moeities was compared to equivalent preparations of untreated virions as follows:

(1) Hemagglutination Activity: Influenza A Hong Kong 168 (IV-AHK) having an oxidized carbohydrate moiety and untreated IV-AHK were cultured in embryonated eggs for 48 hours at 33° C. Hemagglutination activity of virus in the allantoic fluids was determined using chick red blood cells.

(2) Infectivity: Infectivity of IV-AHK was assayed using embryonated chick eggs.

Infectivity of AdV5 was assayed using HeLa cells in culture. [See Vogel et al., Science 126:358-59 (1957); Palmer et al., Advanced Laboratory Techniques For Immunological Diagnosis, Public Health Service Immunological Series No. 6 pgs. 25-62 (1975)]. Results obtained are presented in Table 7.

TABLE 7

BIOLOGICAL ACTIVITY OF VIRUSES HAVING AN OXIDIZED CARBOHYDRATE MOIETY

| VIRUS | Biological Activity | Untreated | Oxidized Carbohydrate Moiety |
|---|---|---|---|
| A Hong Kong 1 A 68 | Hemagglutination activity | $5\times10^4$ | 200 |
| A Hong Kong 1 A 68 | Infectious titer | $10^{12}$ | 10 |
| $AdV_5$ | Infectious titer | $10^6$ | 10 |

As demonstrated in Table 7, hemagglutination activity and infectivity of influenza A Hong Kong 1 A68 was effectively destroyed by oxidation of the carbohydrate moiety. Infectivity of Adenovirus type 5 was also effectively destroyed by such treatment.

11. EXAMPLE: QUANTITATIVE DETERMINATION OF THE TITER OF NEUTRALIZING ANTIBODIES BY DISSOCIATION AND REASSOCIATION OF IMMUNE COMPLEXES

As described above in section 5.2.1.1., in certain instances, such as during an ongoing viral infection, virus or virus fragments could be bound or associated with neutralizing and non-neutralizing antibodies in immune complexes in serum.

In any event, determination of antibody titers before and after dissociation of any antigen-antibody complexes could reveal the presence of such immune complexes in serum samples.

11.1. IMMUNE COMPLEXES DURING ACTIVE CMV INFECTION

As a preliminary experiment, acid dissociation and alkaline reassociation of IgG samples positive and negative for anti-CMV antibodies was performed in order to verify that there were no adverse effects on the titer of free antibodies merely as a result of such dissociation-reassociatin. In order to dissociate complexes, aliquots of diluted serum at pH 7.2 were further diluted 1/50 in buffer containing 0.3 M NaCl, 1% BSA, 10 mM glycine-HCl, pH 2.2, and incubated at 4° C. for 15 minutes. To reassociate any complexes, the pH of the reaction mixture was readjusted to pH 8.1 by addition of neutralizing buffer containing: 0.05 M Borate; 0.010 M glycine; 0.15 M NaCl; 10% Calf serum; 0.1% synperonic PE/L62 adjusted to pH 8.1 with 0.1 M HCl. An ELISA using CMV having an oxidized carbohydrate covalently attached to a reactive amine on a side chain of the polyhydrazidostyrene of the well as described in Section 6.1 above was performed. Results are presented in Table 8.

TABLE 8

| Sample | Antibody Titer-Oxidized Oligosaccharide | |
|---|---|---|
| | Non Dissociated Sample pH 8.1 | Dissociated Reassociated pH 2.2–pH 8.1. |
| IgG positive for anti-CMV | ≧1600 | ≧1600 |
| Control IgG Negative for anti-CMV | <100 | <100 |

As shown in Table 8, dissociation-reassociation had no detectable effect on free anti-CMV antibodies.

Serum samples were obtained from a renal transplant patient before transplantation, during CMV infection, and following recovery. The titer of anti-CMV antibodies in a series of serum samples from this renal patient were determined using an oxidized oligosaccharide covalently attached ELISA as described in Section 6.1 with or without dissociation-reassociation. The antibody titer was also assayed using a conventional adsorption ELISA as described in Section 6.1. Results are presented in Table 9.

TABLE 9

| | Antibody Titer Oxidized Oligosaccharide Covalent ELISA | | Adsorption ELISA |
|---|---|---|---|
| Patient Status | Non-Disassociated pH 8.1 | Disassociated Reassociated pH 2.2–pH 8.1 | Non-Dissociated pH 8.1 |
| No CMV in Urine | 100 | 100 | 100 |
| CMV in Urine | <100 | ≧1600 | ≧12800 |
| No CMV in Urine | >1600 | ≧1600 | ≧12800 |

As demonstrated in Table 9, when CMV was detectable in urine, there was a significant difference in antibody titer measured with or without dissociation-reassociation. In contrast, when no CMV was detectable in urine, there was no significant different in antibody titer with or without disocciation-reassociation. These results strongly suggest the presence of immune complexes in the serum sample when CMV was detected in urine.

11.2. IMMUNE COMPLEXES IN SERUM SAMPLES

Serum samples from unknown blood donors either seropositive or seronegative for HIV were obtained as a gift from Drs. J. C. Chermann and F. Barre-Sanussi of the Institut Pasteur, Paris. The samples had been incubated at 56° C. for 30 minutes to inactivate any HIV virus present.

Antibody titers of aliquots of the sera were assayed as described above using three different assays: (1) Oxidized Oligosaccharide Attached ELISA in which there was no dissociation of the serum sample; (2) oxidized oligosaccharide attached ELISA in which the serum sample was dissociated and then reassociated; and (3) a conventional virus neutralization assay was performed by Drs. Chermann and Barre-Sanussi at the Institute Pasteur. Results obtained are illustrated in Table 10.

TABLE 10

SERA FROM HIV SEROPOSITIVE AND SERONEGATIVE INDIVIDUALS

| | Oxidized Oligosaccharide Attached ELISA Titer | | |
|---|---|---|---|
| Serum No. | Non-Disassociated pH 8.1 | Disassociated Reassociated pH 2.2–pH 8.1 | Neutralization titer |
| 1 | 100 | 100 | 100 |
| 3 | 200 | 100 | <50 |
| 6 | <100 | 100 | <50 |
| 11 | <100 | 100 | 50 |
| 12 | 800 | 400 | 8000 |
| 14 | <100 | 100 | 200 |
| 15 | 200 | 100 | <50 |
| 16 | <100 | 100 | 200 |
| 17 | 100 | 100 | 200 |
| 19 | <100 | 100 | 50 |
| 20 | <100 | 100 | <50 |
| 13 | 800 | 400 | 200 |
| 2 | 400 | ≧1600 | 200 |
| 4 | 800 | ≧1600 | 200 |
| 5 | 100 | 400 | <50 |
| 7 | 800 | ≧1600 | 1000 |
| 8 | 200 | ≧1600 | 200 |
| 9 | 100 | 400 | 50 |
| 10 | 200 | ≧1600 | 200 |
| 18 | 100 | 400 | 100 |

As indicated in Table 10, for some sera, anti-HIV titers obtained with or without dissociation-reassociation were markedly different. These sera were considered to be immune complex positive sera. In other sera, there was no marked difference in anti-HIV titer obtained with or without dissociation-reassociation. These sera were considered immune complex negative.

When all groups of sera including both immune complex positive and negative were grouped together, the titer obtained using the oxidized oligosaccharide ELISA with or without dissociation showed not correlation with the classical neutralization assay titer (correlation coefficient 0.59). When only those sera which were immune complex negative were considered, however, there was a significant positive correlation of antibody titer obtained using the oxidized oligosaccharide ELISA (with or without dissociation-reassociation) and using conventional virus neutralization assay (correlation coefficients 0.99; 0.98 respectively). When only those sera which contained immune complexes were considered, there was a better correlation of titer obtained with the virus neutralization assay and antibody titer using oxidized oligosaccharide ELISA without dissociation-reassociation (correlation coefficient 0.73) than with oxidized oligosaccharide ELISA with dissociation (correlation coefficient 0.48). In either case, however, neither correlation was significant when sera contained immune complexes.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method for protection of an animal or a human from an infection induced by a virus, comprising: administering to an animal or human an effective amount of a vaccine formulation which comprises a virus, viral antigen or fragment thereof having an oxidized oligosaccharide moiety which elicits a protective immune response, in which the oligosaccharide moiety was obtained by oxidation, by means of an agent selected from the group consisting of periodic acid, salts thereof, paraperiodic acid, salts thereof, metaperiodic acid, salts thereof and oxidase enzymes, of an oligosaccharide moiety of a virus, viral antigen or fragment thereof.

2. The method according to claim 1, in which the vaccine formulation further comprises a suitable adjuvant.

3. The method according to claim 1, in which the adjuvant is selected from the group consisting of: aluminum hydroxide, surface active substances, lysolecithin, pluronic polyols, polyanions and peptides.

4. The method according to claim 1 in which the infection is induced by a virus selected from the group consisting of herpesviridae, orthomyxoviridae, hepadnaviridae, parvoviridae, togaviridae, paramyxoviridae, flaviviridae, rhabdoviridae, bunyviridae, reoviridae picornaviridiae and retroviridae.

5. The method according to claim 1, in which the infection is induced by herpes simplex virus I or II.

6. The method according to claim 1, in which the infection is induced by cytomegalovirus.

7. The method according to claim 1, in which the infection is induced by hepatitis virus.

8. The method according to claim 1, in which the infection is induced by rubella virus.

9. The method according to claim 1, in which the infection is induced by measles virus.

10. The method according to claim 1, in which the infection is parainfluenza virus.

11. The method according to claim 1, in which the infection is dengue virus.

12. The method according to claim 1, in which the infection is human lymphoadenopathy-associated virus (LAV, HTLV-III, HIV).

13. The method according to claim 1, in which the infection is an auto-immune disease associated virus.

14. The method according to claim 1, in which the formulation is administered by an intradermal, intramuscular intraperitoneal, intravenous, or subcutaneous route.

* * * * *

UNITED STATES PATENT AND TRADEMARK OFFICE
CERTIFICATE OF CORRECTION

PATENT NO. : 4,965,069

DATED : October 23, 1990

INVENTOR(S) : Quash et al

It is certified that error appears in the above-identified patent and that said Letters Patent is hereby corrected as shown below:

On the title page, please insert the following:

--[73] Assignee: Institut National De La Sante
Et De La Recherche Medicale, Paris, France
and Cytogen Corporation, Princeton, New Jersey--.

Signed and Sealed this

Sixteenth Day of June, 1992

Attest:

DOUGLAS B. COMER

*Attesting Officer*   Acting Commissioner of Patents and Trademarks